(12) United States Patent
Anitua Aldecoa

(10) Patent No.: US 9,326,914 B2
(45) Date of Patent: May 3, 2016

(54) DEVICE FOR EXTRACTING, STORING AND/OR PROCESSING BLOOD OR OTHER SUBSTANCES OF HUMAN OR ANIMAL ORIGIN, AND FOR APPLYING BLOOD COMPOUNDS OR OTHER BIOLOGICAL COMPOUNDS

(71) Applicant: BIOTECHNOLOGY INSTITUTE, I MAS D, S.L., Vitoria (Alava) (ES)

(72) Inventor: Eduardo Anitua Aldecoa, Vitoria (ES)

(73) Assignee: BIOTECHNOLOGY INSTITUTE, I MAS D, S.L., Vitoria (Alava) (ES)

( * ) Notice: Subject to any disclaimer, the term of this patent is extended or adjusted under 35 U.S.C. 154(b) by 0 days.

(21) Appl. No.: 13/935,100

(22) Filed: Jul. 3, 2013

(65) Prior Publication Data

US 2014/0010740 A1   Jan. 9, 2014

(30) Foreign Application Priority Data

Jul. 3, 2012   (ES) .................................. 201200691

(51) Int. Cl.
*B01L 99/00*   (2010.01)
*A61J 1/14*   (2006.01)
*A61B 5/15*   (2006.01)
*A61B 5/153*   (2006.01)
(Continued)

(52) U.S. Cl.
CPC ............. *A61J 1/1406* (2013.01); *A61B 5/1433* (2013.01); *A61B 5/1438* (2013.01); *A61B 5/153* (2013.01); *A61B 5/15003* (2013.01); *A61B 5/154* (2013.01); *A61B 5/150236* (2013.01); *A61B 5/150244* (2013.01); *A61B 5/150259* (2013.01);
(Continued)

(58) Field of Classification Search
CPC ... A61M 5/14244; A61M 5/19; A61M 5/284; A61M 5/31596; A61M 5/2053; A61M 5/24; A61M 5/322; A61M 2005/31508; A61M 5/1413; A61M 5/14216; A61M 5/145; A61M 5/14566; A61M 5/28; A61M 5/282; A61M 5/5013; A61M 5/5066; B01L 2200/16; B01L 2400/0478; A61B 5/150755
USPC ........................................... 422/570; 604/110
See application file for complete search history.

(56) References Cited

U.S. PATENT DOCUMENTS 4,906,231 A * 3/1990 Young ........................... 604/110
5,174,301 A   12/1992 Sarstedt
(Continued)

FOREIGN PATENT DOCUMENTS

| EP | 2077115 A1 | 10/2007 |
|---|---|---|
| ES | 8103960 A1 | 7/1981 |
| WO | 2006058435 A2 | 6/2006 |

OTHER PUBLICATIONS

International Search Report issued Feb. 11, 2014, in corresponding Spanish Application No. 201200691.

*Primary Examiner* — Dennis M White
(74) *Attorney, Agent, or Firm* — Browdy and Neimark, PLLC

(57) ABSTRACT

Device (1a, 1b, 1c, 1d; 40) for extracting, storing and/or processing blood or other substances of human or animal origin, and for applying blood compounds or other biological compounds, which comprises a body (2; 41) inside which a piston (3; 42) is capable of moving longitudinally and is separable at least in part, where the body (2; 41) is provided with an internal space (9; 51) that may be connected to the outside by means of a conduit (6; 50) at a first end (4; 48) of the body (2; 41), where the body (2; 41) and the piston (3; 43) may be blocked longitudinally in at least one position to allow the creation of different degrees of vacuum. The device has multiple uses and is extremely versatile.

19 Claims, 14 Drawing Sheets

(51) Int. Cl.
  *A61B 5/154* (2006.01)
  *A61M 5/315* (2006.01)
(52) U.S. Cl.
  CPC ..... *A61B 5/150351* (2013.01); *A61B 5/150572* (2013.01); *A61B 5/150755* (2013.01); *A61B 5/150908* (2013.01); *A61M 5/31515* (2013.01); *A61M 2005/31508* (2013.01); *B01L 2200/16* (2013.01); *B01L 2400/0478* (2013.01)

(56) References Cited

U.S. PATENT DOCUMENTS

| | | |
|---|---|---|
| 2002/0156396 A1 | 10/2002 | Tiu |
| 2008/0188828 A1* | 8/2008 | Reynolds et al. .............. 604/520 |
| 2010/0025342 A1* | 2/2010 | Morimoto et al. ............ 210/787 |
| 2011/0083978 A1 | 4/2011 | Lavi |

* cited by examiner

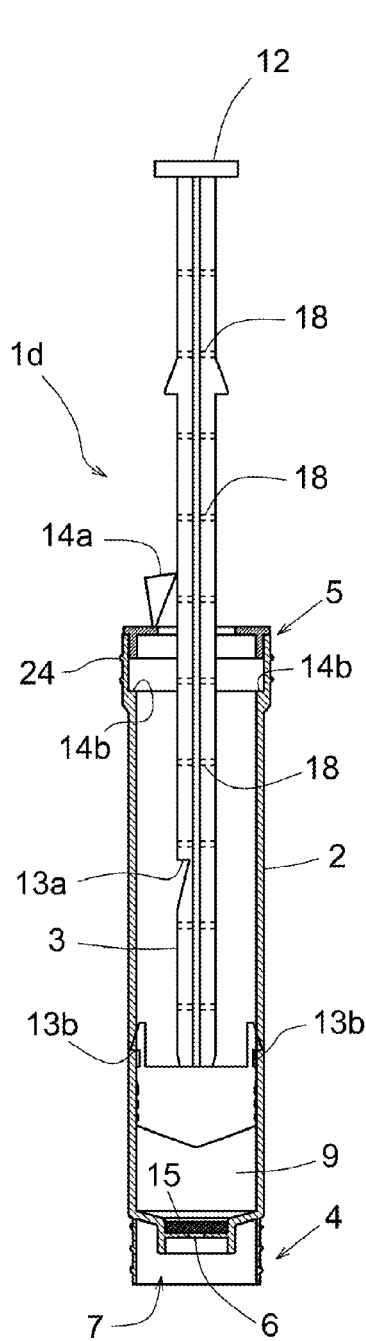
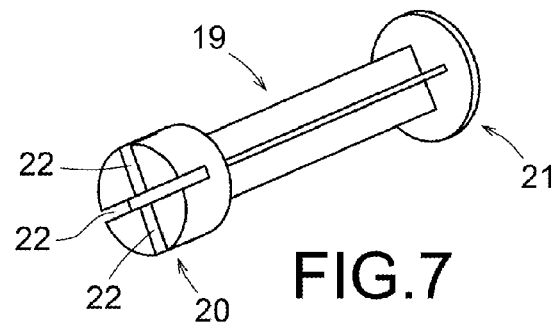
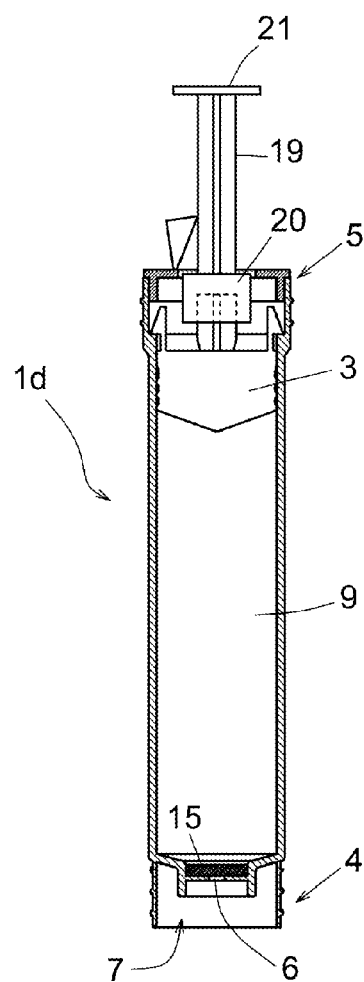
FIG.6
FIG.7
FIG.8

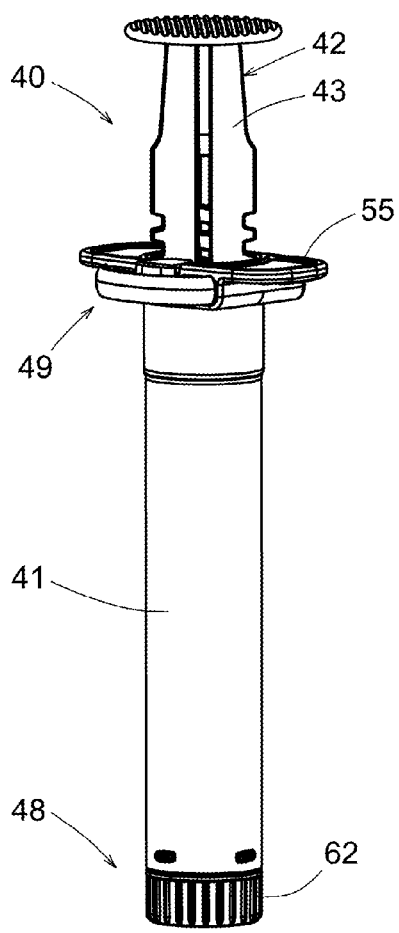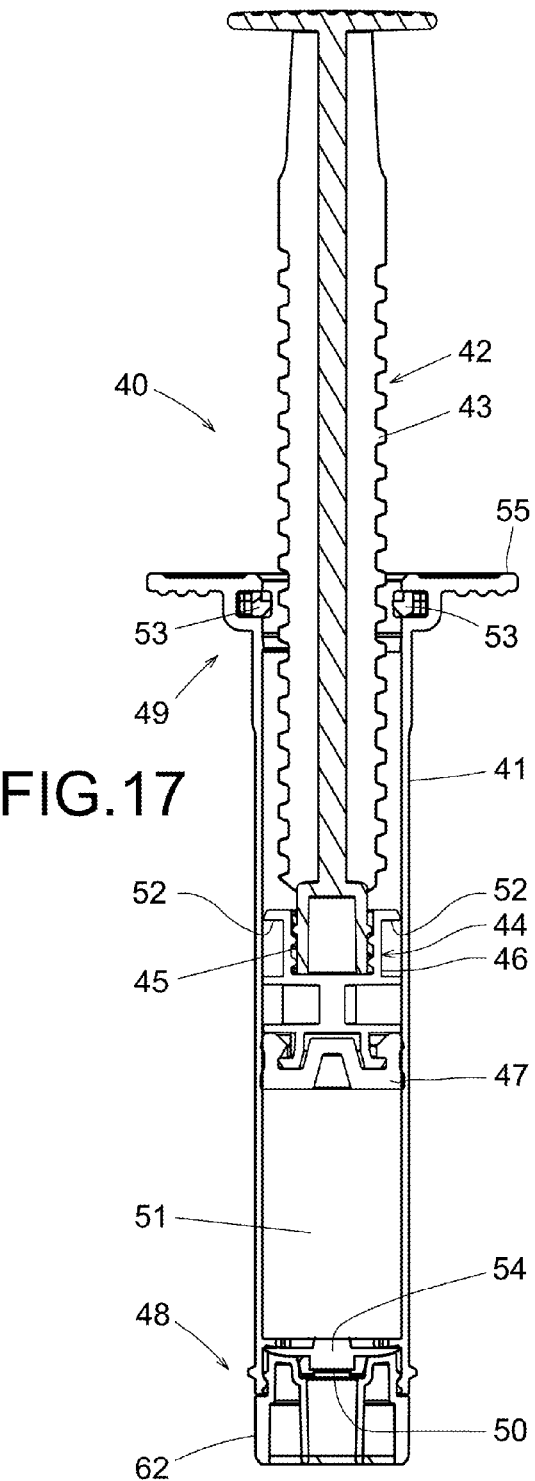
FIG. 16
FIG. 17

DEVICE FOR EXTRACTING, STORING AND/OR PROCESSING BLOOD OR OTHER SUBSTANCES OF HUMAN OR ANIMAL ORIGIN, AND FOR APPLYING BLOOD COMPOUNDS OR OTHER BIOLOGICAL COMPOUNDS

TECHNICAL FIELD

The invention relates to a device for extracting, storing and/or processing blood or other substances of human or animal origin, and for applying blood compounds or other biological compounds. Specifically, the invention relates to a single device with which blood may be extracted, in which the blood may be processed, the blood or substances obtained stored, and from which the substances obtained may be applied.

PRIOR ART

The extraction of small amounts of blood from a patient or animal and its subsequent processing for the appropriate therapeutic purpose is generally performed using vacuum tubes, closed with a perforable sealing cap. A butterfly needle is connected to the vacuum tube and is inserted into the patient's vein. Once it is extracted to the vacuum tubes, blood is processed using methods that vary according to the medical application. For example, in many medical applications blood is centrifuged so that it is separated into different fractions. Said centrifuging is generally carried out in the vacuum tubes into which the blood was first extracted. Then, the blood compounds obtained by centrifugation or, in general, the processed blood compounds, usually have to be transferred to other containers for further processing or storage. For example, in the case of certain centrifuged compounds (such as platelet-rich plasma, for instance to be applied to the patient at a later stage) said compounds may have to be transferred to a syringe, in the event that they need to be applied to the patient or another medium.

The transfer of blood or blood compounds from one container or device to another always involves the risk of the blood or blood compound suffering some kind of contamination, e.g., a bacterial contamination.

An additional drawback of vacuum tubes is that they tend to gradually lose their vacuum. As a result, tubes that have been stored for a period of time before being used to receive blood during an extraction may not be capable of storing as much blood as when they were first supplied —due to the degree of vacuum in their interior having been reduced—. Also, long stored tubes may have been contaminated as a result of air potentially leaking into them.

The invention aims to offer a device that solves at least one of the aforementioned problems.

In other words, one of the objectives of the invention is to provide a versatile device, offering a variety of uses and thus reducing the number of transfers between the containers usually required in procedures involving extracting, processing and storing blood or blood compounds.

It would also be desirable to provide a device that reduces or eliminates the negative results caused by the loss of vacuum over time in blood-extraction and blood-storage devices.

BRIEF DESCRIPTION OF THE INVENTION

It is an object of this invention to provide a device for extracting, storing and/or processing blood or other substances of human or animal origin, and for applying blood compounds or other biological compounds, which comprises a body inside which a piston is capable of moving longitudinally. The body is provided with a first end in which there is a conduit that connects an internal space of the body located between the piston and the conduit with the outside of the body. The body also comprises a second end through which the piston projects outward. The internal space of the body is hermetically separated from the second end by means of the piston. The movement of the piston towards the first end where the conduit is situated allows the contents of the internal space to be expelled. In contrast, the movement of the piston towards the second end, opposite the conduit, allows the vacuum in the internal space to be created.

In accordance with the invention, the aforementioned piston-body-based device presents the specific feature that at least part of the piston is capable of being separated from the rest of the device so that the piston does not project out of the body. In addition, the device presents mechanisms for the one-way blocking of the piston, with the result that in the event of being blocked, the piston cannot move towards the first end of the body, although it may move back towards the second. The device also comprises a sealing member located on the first end, specifically in order to close the conduit of the first end of the body in a sealed manner in the event of a needle being inserted into said conduit. In other words, the sealing member guarantees that the conduit forms a sealed intake for a needle.

The aforementioned characteristics make the device extremely versatile. Firstly, the device may be used as a container into which the blood of a patient is extracted, provided that vacuum has been created in the device beforehand with the aid of the piston and the piston has been blocked so that the vacuum is held at the required level. Additionally, when at least one part of the piston is separated from the rest of the device, the device may function as a tube for storing compounds and even for processing compounds (for example, in a centrifuging process). Furthermore, the piston may be unblocked to allow it to move once more towards the first end, as a result of which the device may also function as a syringe. An additional advantage is the fact that, in the event that the device has various points at which the piston is blocked longitudinally in relation to the body, the degree of vacuum inside the device is adjustable.

The provision of a device with the ability to be converted from an initial body-piston unit to a tube-type container and vice versa results in significant improvements in some medical processes. In the first place, it allows the processes to be performed with a smaller number of devices due to the fact that the inventive device presents a number of uses. Additionally, for identical reasons the number of transfers required between different devices is reduced, thus increasing biosafety.

An additional advantage of the invention is that the device performs optimally when used as an extraction or storage container, due to the fact that the device is provided with a piston that allows creating vacuum at any given moment and with a sealed internal space. Vacuum may be created at the exact moment that the device is to be used, guaranteeing that the level of vacuum is optimal when the device is to be used and making the level of vacuum adjustable. And, in the event that air enters the device, vacuum may be created once more in order to overcome said problem.

The sealing member may be internal to the body. In other words, it may be present at all times. Alternatively, the sealing member may be external to the body and connected to and disconnected from the body. In other words, it may not be present in the device at all times. Additionally, the sealing member may be perforable so that it provides an airtight seal at all times and the device may operate without a needle. Alternatively, the sealing member can take the shape of a ring with a through-hole for the insertion of a needle, so that it is airtight only when a needle is inserted through said hole and fits against the ring.

BRIEF DESCRIPTION OF THE DRAWINGS

Details of the invention can be seen in the accompanying non-limiting drawings:

FIG. 6 shows a sectional view of a fourth embodiment of a device according to the invention.

FIG. 7 shows an embodiment of a pusher member.

FIG. 8 shows a sectional view of the device of FIG. 6, to which the pusher member of FIG. 7 has been connected.

FIG. 16 shows an eighth embodiment of the device according to the invention.

FIG. 17 shows a sectional view of the aforementioned device, according to a vertical section plane comprising the longitudinal central axis of the device.

DETAILED DESCRIPTION OF THE INVENTION

Figure 1:
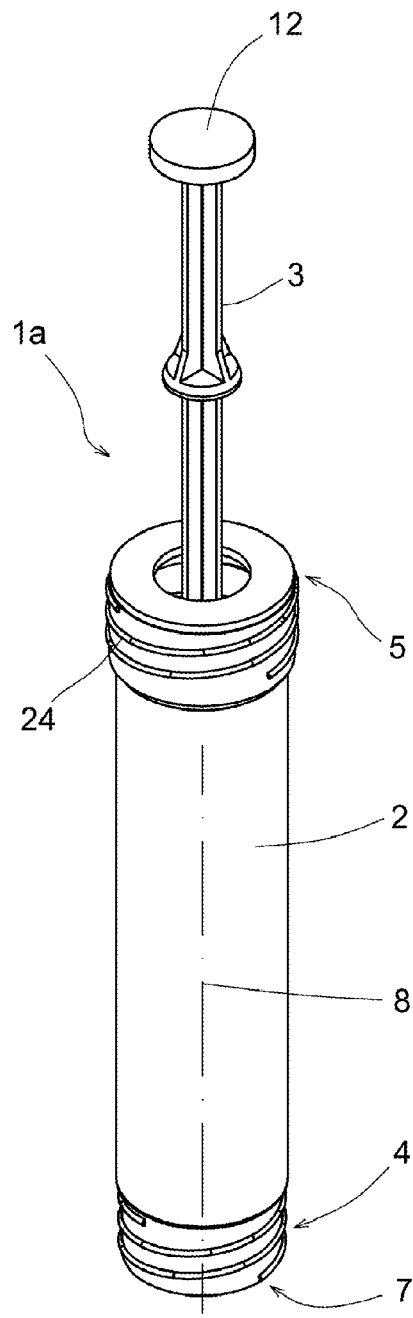
FIGS. 1 and 2 show two perspective views of a first embodiment of the device according to the invention.
Figure 2:
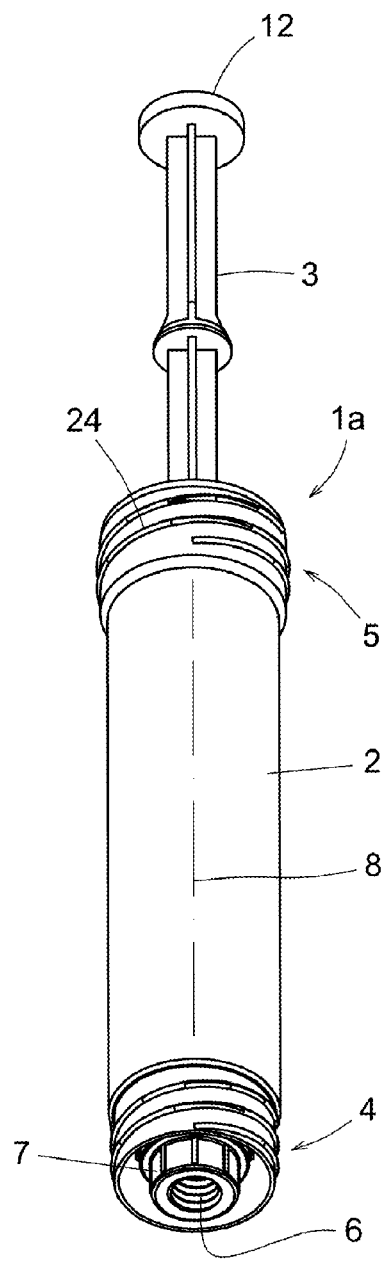

FIGS. 1 and 2 show two perspectives of a first embodiment of a device (1a) according to the invention, for extracing, storing and/or processing blood or other substances of human or animal origin, and for applying blood compounds or other biological compounds. Said device (1a) comprises a body (2) inside which a piston (3) is capable of moving longitudinally. The body (2) is provided with a first end (4) and a second end (5). The piston (3) projects out through the second end (5) and delimits, in a sealed manner inside the body (2), an internal space (not shown in the figures). The internal space is connected to the exterior by means of a conduit (6) situated in the area of the first end (4). The first end (4) preferably ends in a connector (7) that allows the device (1a) to be coupled to other devices. An example of an applicable connector (7) is a Luer lock or similar connection.

Figure 3:
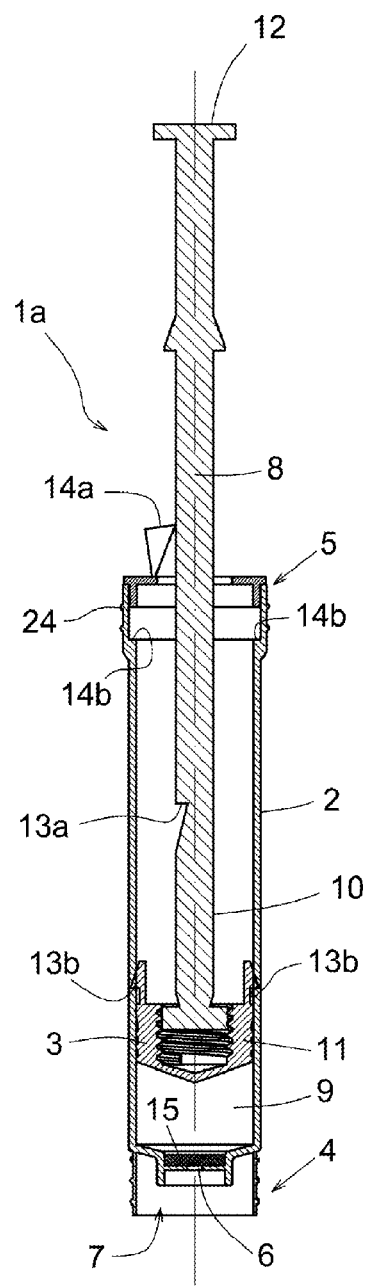
FIG. 3 shows a sectional view of the device, according to a vertical section plane passing through the longitudinal central axis of the device.

FIG. 3 shows a sectional view of the device (1a) of the preceding figures. The section has been formed according to a vertical section plane that contains the longitudinal central axis (8) of the body (2). As shown in the figure, an internal space (9) is delimited inside the body (2), between the piston (3) and the conduit (6). The piston (3) fits tightly to the internal walls of the body (2) to provide a sealed separation between the internal space (9) and the second end (5) of the body (2). In other words, the piston (3) hermetically or tightly seals the upper area (in accordance with the position of the device in the figure) of the internal space (9). Opposite the piston (3) is the conduit (6), which connects the internal space (9) of the body (2) to the outside of the body (2).

At least part of the piston (3) is capable of being separated from the rest of the device so that the piston (3) does not project out of the body (2). This feature makes the device a versatile tool and also allows a single piston (3) to be shared by or used with various bodies (2). In this specific embodiment, the piston (3) comprises a rod (10) and a head (11), where the rod (10) is fixed to the head (11) by means of a joint that may be disconnected and connected, in this case by means of a threaded joint. Said disconnectable and connectable joint allows the rod (10) to be released from the head (11) when necessary, and to be re-connected when required. This allows the device to be used as follows: first, with the rod (10) connected to the head (11), the rod (10) may be pulled backwards—for instance by pulling on an operable area (12) generally comprised in the rod (10)—to create a vacuum; a biological compound (for example, blood extracted from a patient) may then be transferred by vacuum to the device; the rod (10) may then be disconnected and removed to allow the device to be used as a tube, e.g. for storing the compound or for processing the compound (for instance, by centrifugation); later, the rod (10) may be re-connected so that the device can be used as syringe, i.e., in order to allow pushing the piston (3) towards the conduit (6) and expelling the compound stored in the internal space (9). Furthermore, the provision of a joint that may be disconnected and connected allows the rod (10) to be reused with other devices and the vacuum to be repeated or adjustable.

Additionally, the piston (3) comprises at least one blocking surface (13a, 13b). In turn, the body (2) comprises at least one blocking surface (14a, 14b) adapted to come into contact with a blocking surface (13a, 13b) of the piston (3). Said contact between the corresponding blocking surfaces (13a, 14a; 13b, 14b) is such that it provides a one-way blocking of the piston (3), as a result of which resistance is offered to the moving of the piston (3) towards the first end (4), while allowing the piston (3) to move back towards the second end (5).

The device (1a) further comprises an internal and perforable sealing member (15) that allows closing the conduit (6) of the first end (4) of the body (2) in a sealed manner in the event of a needle or similar member being inserted in said conduit (6). Because the sealing member is internal and perforable, it is permanently present inside the body (2) and sealingly closes the conduit (6) permanently. The internal space (9) is only communicated with the outside when a needle (such as a blood extraction butterfly needle) is inserted and perforates the sealing member (15). As a result of permanent sealing, vacuum may be created in the internal space (9) at any time simply by pulling the piston (3) back. This allows recovering vacuum conditions in the event of a slight loss of vacuum—caused, for example, by having stored the device in unsuitable Conditions—. In addition, the provision of an internal and perforable sealing member provides a permanently sealed, integrated device that can be used, for instance, as a container to which blood have blood extracted, as a container to/from which have plasma fractions transferred, etc.

The combination of the aforementioned characteristics makes the device extremely versatile. Firstly, in normal conditions and by pulling the piston (3) back, vacuum may be created in the internal space (9) of the body (2) allowing the device (1a) to be used for receiving a substance by vacuum effect (for example, for receiving blood from a patient's vein). Secondly, when the piston (3) is blocked in the body (2), i.e. prevented from advancing towards the first end (4), part of the piston (3) may be separated to avoid the rest of the piston (3) from projecting out of the body (2), allowing the device (1a) to then be used as a tube, for example for storage, centrifugation, etc.

As shown in the figure, it is particularly interesting that a blocking surface (13b) of the piston (3) is specifically comprised in the head (11) of the piston (3). This enables the rod (10) to be disconnected from the piston (3) while the blocking between the head (11) and the body (2) is maintained by said blocking surface (13b) of the head (11) being engaged on a corresponding blocking surface (14b) of the body (2). The fact that the blocking of the head (11) is maintained when the rod (10) is removed allows the rod (10) to be used successively in various devices and enables all the devices, once the rod has been removed for use in the next device, to be kept in identical conditions until all of the devices are ready to be processed.

Figure 4:
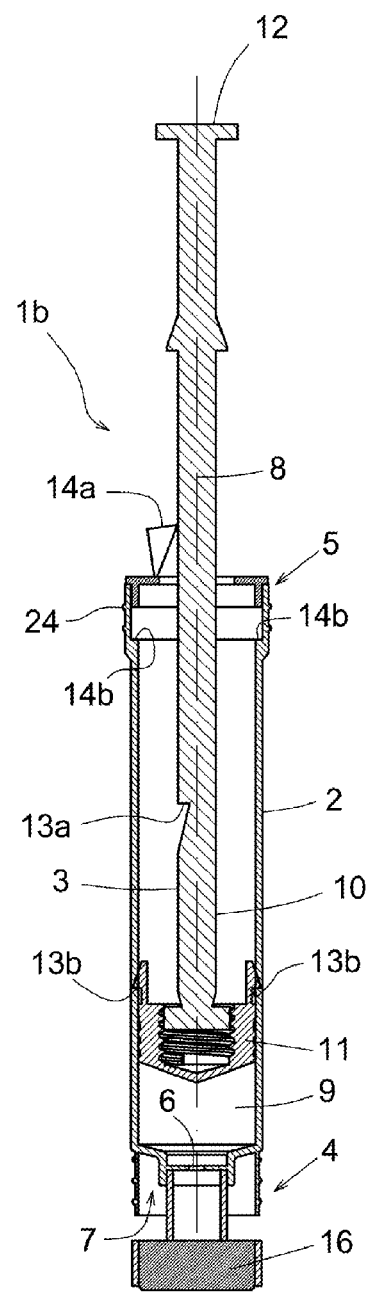
FIG. 4 shows a sectional view of a second embodiment of a device according to the invention.

FIG. 4 shows a second embodiment of the device (1b) according to the invention. In this case, the sealing member (16) is perforable and external, capable of being connected to the first end (4). For example, the sealing member (16) is a septum accessory. The fact that the sealing member (16) is external and may be connected and disconnected means that when the sealing member (16) is not present other accessories may be connected to the first end (4) to allow the device (1b) to perform other functions. For example, a conventional syringe needle may be connected to the first end (4) to allow the device (1b) to be used as a syringe.

Figure 5:
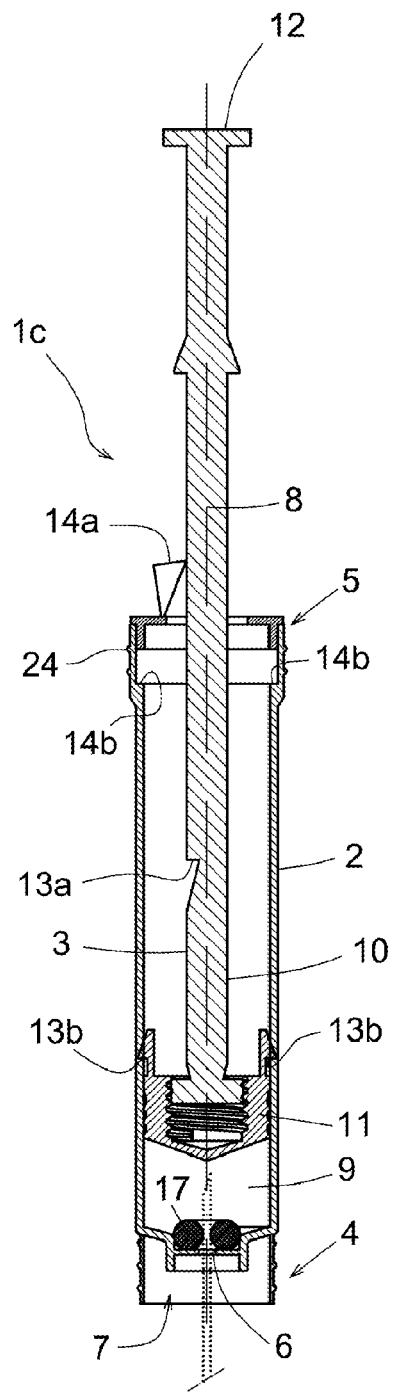
FIG. 5 shows a sectional view of a third embodiment of a device according to the invention.

FIG. 5 shows a third embodiment of a device (1c) according to the invention. In this case, the sealing member (17) is internal and ring-shaped, and is located at the conduit (6). The internal space (9) is connected at all times with the outside by the conduit (6), and it is only when a needle is introduced into the conduit and the external walls of the needle come into contact in a sealed manner against the sealing member (17) that the internal space (9) is sealingly insulated from the outside. With the aim of illustrating this aspect, a needle drawn with dotted lines is shown inserted through the sealing member (17). This embodiment is therefore characterised in that the vacuum can only be created in the internal space (9) when a needle is inserted through the conduit (6). The advantage of this embodiment is that only a very small amount of effort is required to insert the needle, as there is no need to perforate a perforable member. This allows for instance for the needle not to require a sharp tip. In addition, provided that the degree of interference between the ring-shaped seal and the needle is configured properly, the interior of the device can be just as airtight as or even more airtight than it would be using a perforable member. Furthermore, in the event that the device is used repeatedly, the device (1b) suffers only very minimal wear and remains equally capable of acquiring airtightness.

Preferably, the piston (3) is capable of moving rotationally inside the body (2). In addition, at least one blocking surface (14a, 14b) of the body (2) and at least one blocking surface (13a, 13b) of the piston (3) are disposed in such a way that blocking is caused only in certain rotational positions of the piston (3) in relation to the body (2), the piston (3) being free in relation to the body (2) in the remaining rotational positions. This allows the user to lock and unlock the advance of the piston (3) towards the first end (4) by making a simple manipulation. When the user wishes to use the device as a storage and processing tube, they pull the piston back and rotate it until blocking takes place. When the user wishes to use it as syringe they rotate the piston until it is unblocked and can advance freely towards the first end.

FIG. 6 shows a fourth embodiment of a device (1d) according to the invention. In this case, the piston (3) comprises at least one breakable area (18) so that it may be manually broken into separate parts. In other words, some parts of the piston (3) may be separated from the rest of the piston (3) in a breakable and non-reconnectable manner. This allows for an embodiment that avoids re-using of the piston (3), which in certain circumstances may be of interest, for instance for preventing cross contamination between patients.

For this embodiment the device (1d) features an accessory or pusher member (19), an example of which is shown in FIG. 7. Said pusher member (19) comprises a first area (20) capable of pushing the piston (3) in order to overcome the resistance to the advance of the piston (3) offered by the blocking between at least one blocking surface (13a, 13b) of the piston (3) and the corresponding blocking surface (14a, 14b) of the body (2) and therefore to cause the advance of the piston (3) towards the first end (4). Pushing may be exerted, for instance, on a second area (21) adapted for this purpose. The pusher member (19) allows the device (1d) to be used as a syringe once the piston (3) has been broken.

Preferably, the first area (20) of the pusher member (19) is capable of being connected to the piston (3) in such a way that it can cause rotation of the piston (3). For example, in this embodiment the first area (20) presents grooves (22) having a complementary shape to that of the broken piston (3). The broken piston may thus be inserted to a slight extent in said grooves (22), and if a torque is applied to the pusher member (19) said torque is transferred to the piston (3). This allows the present embodiment to feature a piston (3) capable of being rotated. As a result, the piston (3) may also be designed, as previous embodiments, to be blocked in some rotational positions and unblocked in others.

In addition, the first area (20) of the pusher member (19) may be shaped complementarily to the piston (3) so that the connection between the pusher member (19) and the piston (3) is in fact achieved by the pushing force itself. In other words, the positioning of the pusher member (19) behind the piston (3) and the pushing of the pusher member (19) not only causes the advance of the piston (3) but also enhances the connection between both parts (3, 19).

Additionally, the first area (20) of the pusher member (19) may be formed having a mechanical connection to the piston (3) so that the connection between the pusher member (19) and the piston (3) allows the piston (3) not only to be pushed towards the first end (4) but also to be pulled back towards the second end (5). This allows for vacuum to be created inside the device at any given moment, if necessary.

Figure 9:
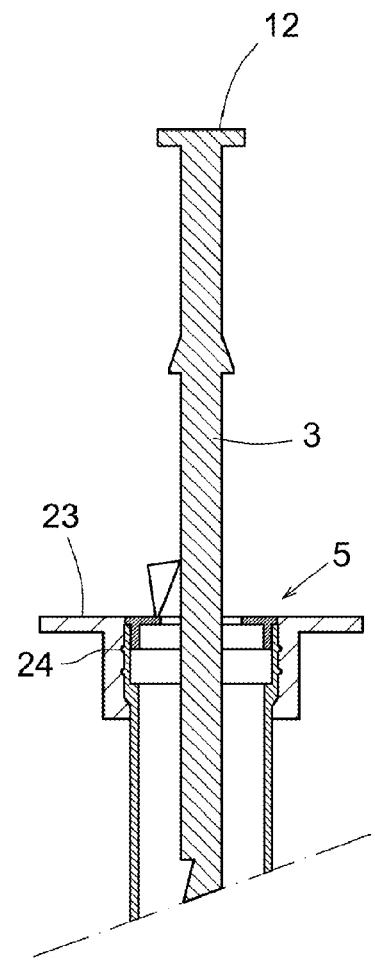
FIG. 9 shows a fifth embodiment of the device according to the invention.

FIG. 9 shows an additional member that may be comprised in the devices (1a, 1b, 1c, 1d). Said additional member is a handle (23) located on the second end (5) to enable the action of causing the piston (3) to move back towards said second end (5). The handle (23) is connected to the rest of the body (2) in a disconnectable and connectable manner, preferably by means of a thread (24), as shown in the figure. This allows the handle (23) to be disconnected from the body (2) once vacuum has been created in the internal space (9) and the piston (3) and the body (2) have been blocked, so that the handle (23) can be used with other devices, whilst maintaining the blocking between the piston (3) and the body (2).

Figure 10:
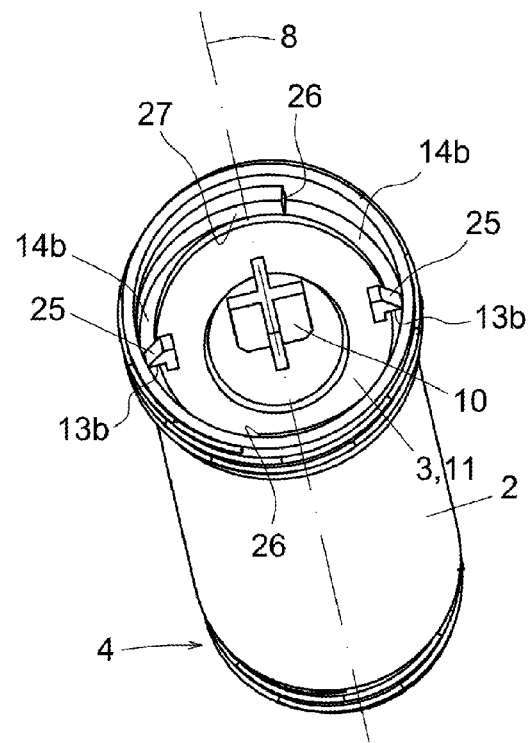
FIGS. 10 to 12 show a sixth embodiment of the device according to the invention.
Figure 11:
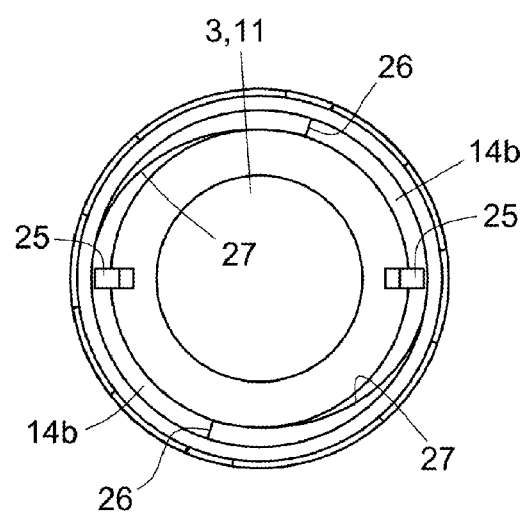
Figure 12:
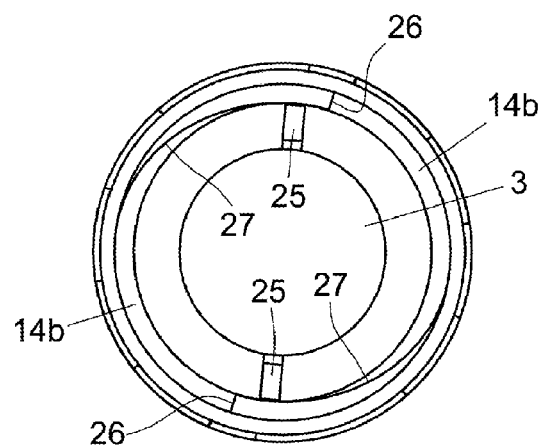

FIGS. 10, 11 and 12 show an additional optional feature of the invention, according to which the piston (3) comprises one or more tabs (25)—two, in the figures—that protrude radially from the piston (3). To aid understanding of the figures, the axis of the piston (3) is shown only partially in FIG. 10, and is fully omitted from FIGS. 11 and 12. The tabs (25) provide or act as a blocking surface (13b) of the piston (3). In addition, the corresponding blocking surface (14b) of the body (2) takes the form of a transversal seating surface, transversal being understood as the surface having a component in the radial direction of the body (2). The piston (3) is blocked in relation to the body (2) when the tabs (25) are supported on the blocking surfaces (14b), as shown in FIGS. 10 and 11. The body (2) also comprises internal walls (27), the distance of which from the longitudinal central axis (8) decreases in the direction of rotation in which the piston (3) must rotate in order to be unblocked from the body (2) (which in the case shown in the figure is clockwise). Thus, as can be seen, if starting from a blocked situation such as that of FIG. 11 the rotation of the piston (3) is caused in a blocking direction (clockwise), the tabs (25) rotate in contact with the internal walls (27), and decreasing distance between the internal walls (27) and the longitudinal central axis (8) causes the tabs (25) to flex inwards. A situation such as the one shown in FIG. 12 is eventually reached where the tabs (25) are flexed sufficiently inwards for the blocking surface (14b) of the body (2) to be freed, the piston (3) thus becoming unblocked from the body (2) and being able to advance towards the first end (4).

The invention also contemplates an optional technical feature applicable to those cases in which the rod (10) and the head (11) of the piston (3) are threaded to each other. Specifically, the body (2) may present at least one stopper member (26) against an area of the head (11) is capable of coming into contact when the head (11) rotates in an opposite direction to the tightening direction of said threaded joint. As a result, when the user wishes to unscrew the rod (10) from the head (11) and for this purpose causes the rotation of the rod (10) in the opposite direction to the tightening direction, the head (11) eventually encounters the stopper member (26), who retains the head (11) and prevents it from rotating in conjunction with the rod (10), therefore allowing the rod (10) to be unthreaded from the head (11). FIGS. 10, 11 and 12 show an embodiment of this stopper member (26), consisting in a wall formed on a radial plane and against which the head (11) comes into contact when it rotates around the longitudinal central axis (8). Particularly, the area of the head (11) that contacts the stopper member (26) is specifically comprised in a tab (25). In other words, it is the tab (25) that performs the double function of longitudinally blocking the head (11) and of restricting the rotation of the head (11) in an opposite direction to the one in which the rod (10) is tightened.

Figure 13A:
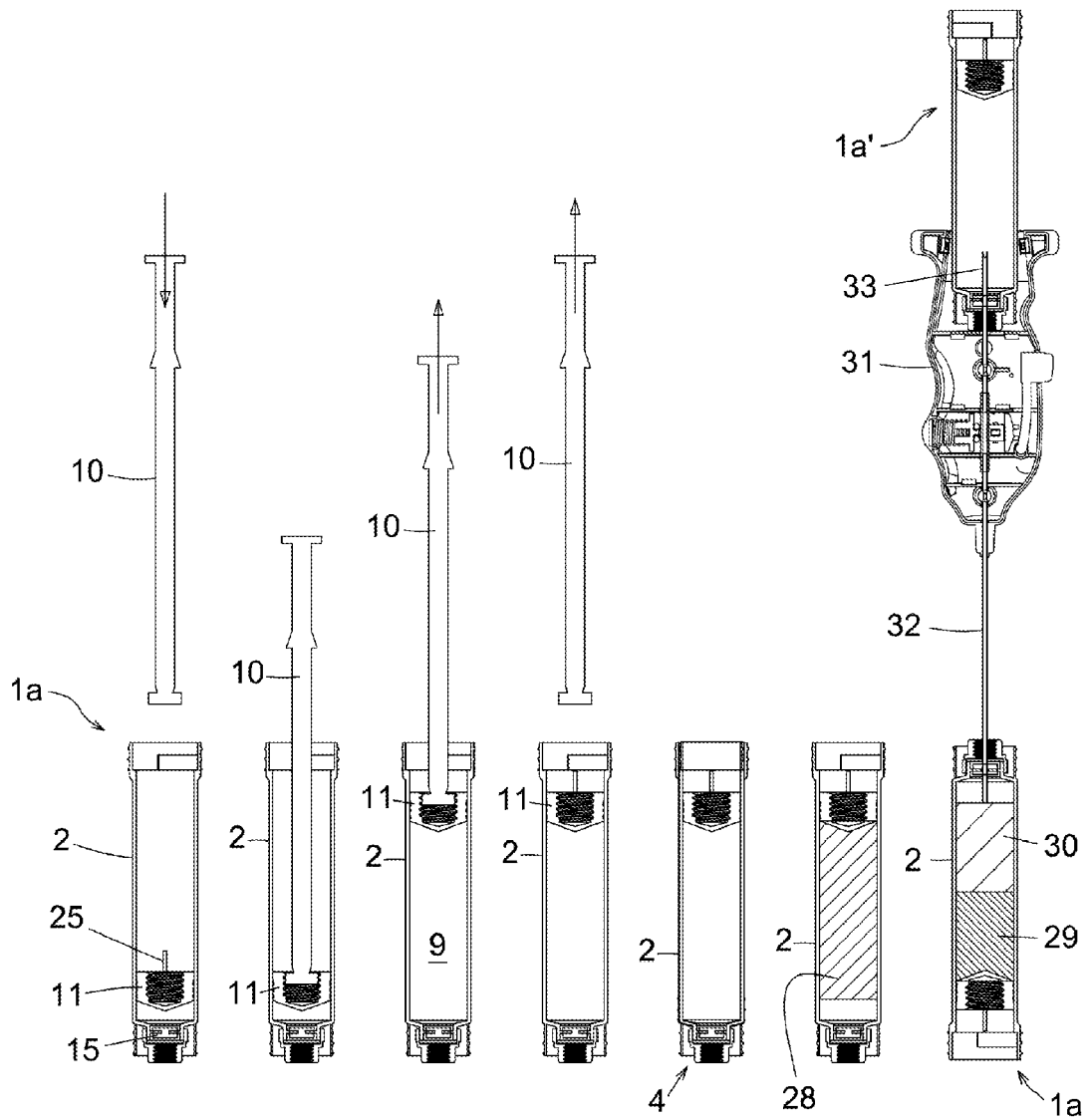
FIGS. 13A and 13B show a sequence for the preparation of a plasma rich in growth factors (PRGF) in which the device of FIG. 1 is used.
Figure 13B:
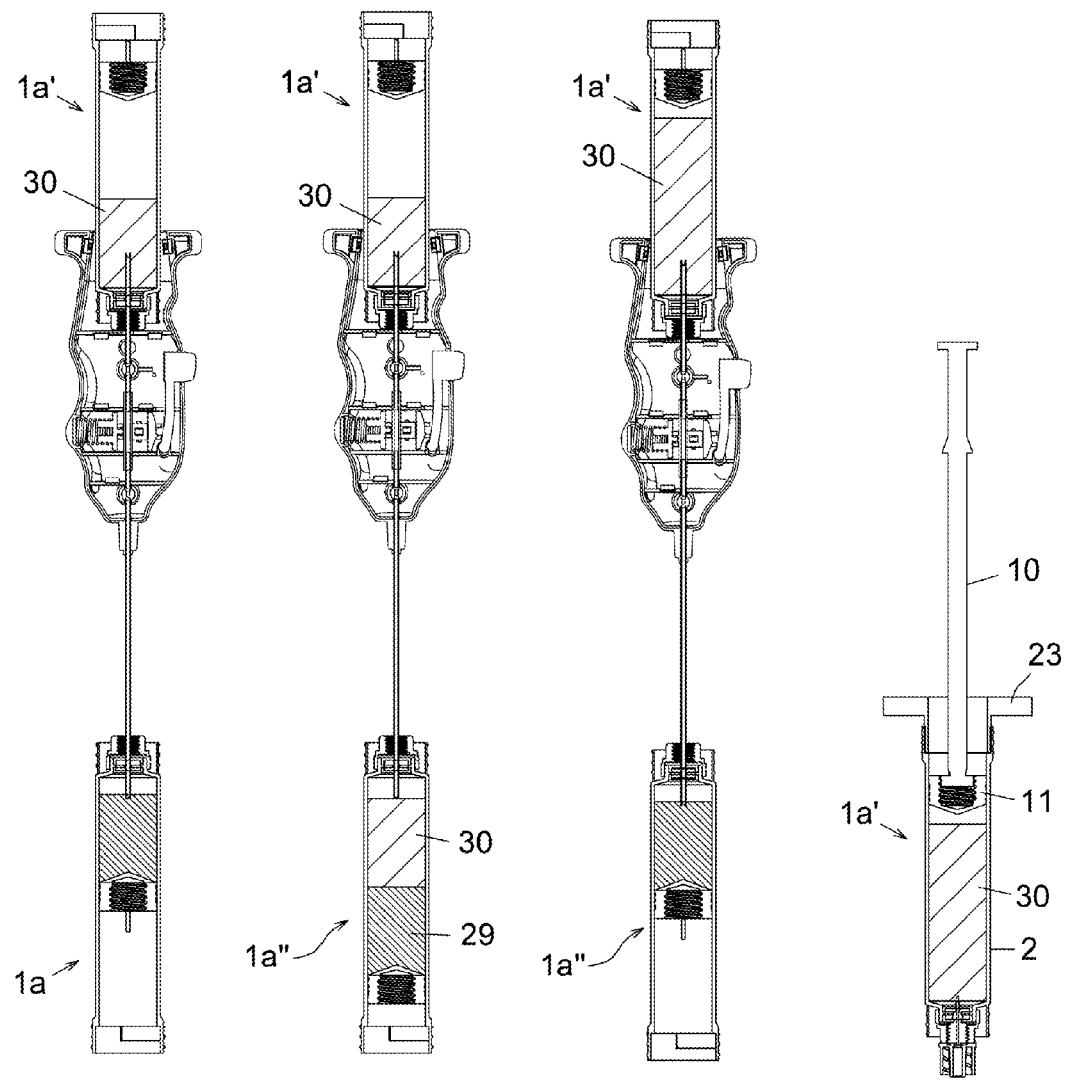

FIGS. 13A and 13B show an example of use of a device according to the invention, which provides an understanding of its extreme versatility. A sequence for the preparation of a plasma rich in growth factors (PRGF) in which the device (1a) of FIG. 1 is used is shown. The sequence starts with a body (2) inside which the head (11) of a piston (3) is housed. In a first step, the rod (10) of the piston (3) is threaded on to said head (11). The rod (10) is then pulled back, causing the head (11) to move inside the body (2) and a vacuum to form in the internal space (9) of the body (2). When the vacuum has been created, the rod (10) is unthreaded from the head (11), therefore obtaining a tube-shaped device (1a) provided with inner vacuum conditions. Blood is then extracted from the vein of the patient towards the internal space (9) of the device (1a), for which a suitable accessory is connected to the first end (4) of the body (2). When the body (2) has been filled with blood (28), separation of the blood into different fractions, among them a fraction (29) of red globules and a fraction (30) of platelet-rich plasma, is carried out for instance by centrifuging the device (1a) in suitable conditions. The device (1a) is then connected to a second device (1a'), by means of an intermediate shutter device (31), vacuum having been created inside the second device (la') beforehand. The shutter device (31) is capable of opening and closing the passage between respective needles (32, 33), which are connected to each device (1a, 1a'), with the result that the passage of substances between the devices (1a, 1a') may be enabled or prevented. The needle (32) of the example, which is connected to the first device (1a), does not have a sharp tip as the sealing member (15) has been perforated beforehand by a needle with a tip (this prior needle and perforating step are not shown in the figures). When correctly operated, the shutter device (31) then opens the passage between the needles (32, 33) and allows the transfer by vacuum effect of the fraction (30) of platelet-rich plasma of the first device (1a) to the second device (1a'), as shown in the first step of FIG. 13B. The procedure is then repeated with a third device (1a") containing blood fractions (29, 30), with the result that the second device (1a') contains fractions (30) of platelet-rich plasma originating from two devices (1a, 1a"). Finally, the second device (1a') is removed and the rod (10) of the piston (3) and the handle (23) are both connected, as a result of which the second device (1a') is ready to be used as a syringe (a needle is not shown) as soon as the head (11) of the piston (3) is unblocked from the body (2).

Figure 14:
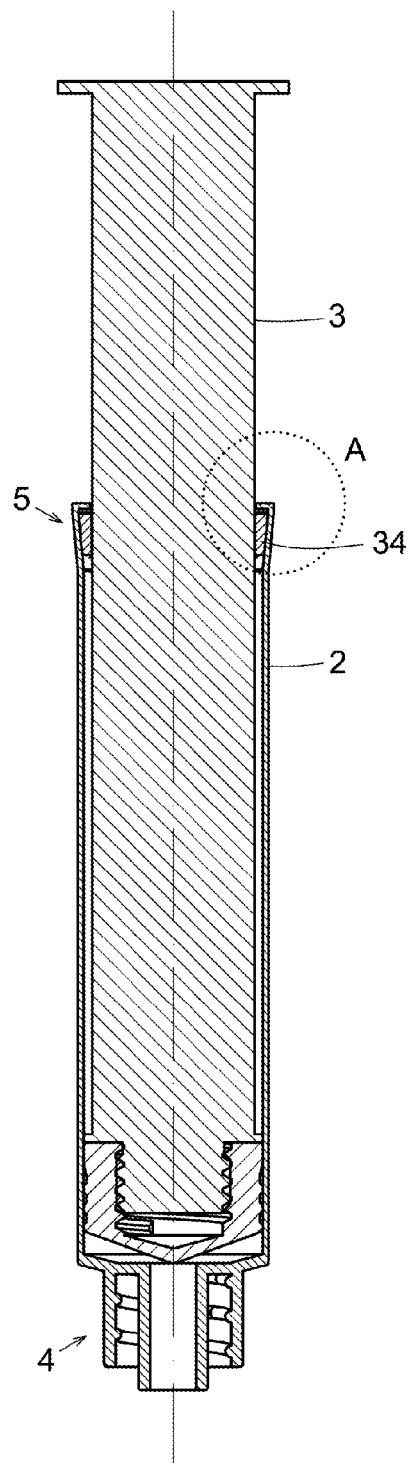
FIG. 14 shows a seventh embodiment of the device according to the invention.
Figure 15:
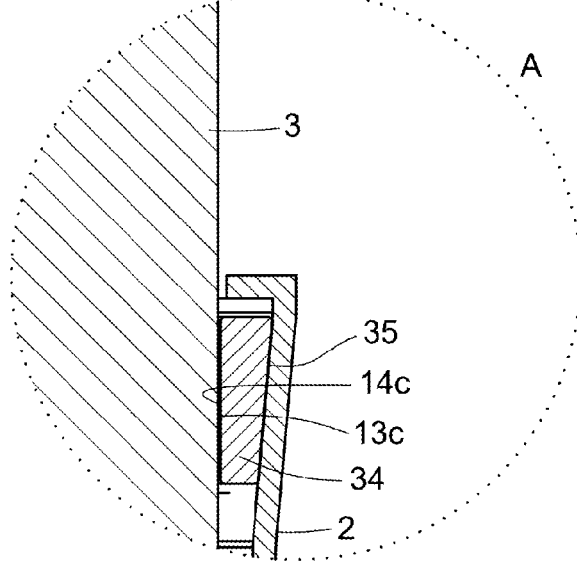
FIG. 15 shows an enlarged view of detail A of FIG. 14.

FIGS. 14 and 15 show an alternative embodiment of blocking surfaces according to the invention. In this case, the piston (3) comprises a blocking surface (13c) capable of coming into contact with a blocking surface (14c) located in the internal wall of an intermediate conical part (34) of the body (2). The intermediate conical part (34) presents limited longitudinal mobility in relation to the piston (3) and in relation to the rest of the body (2). When the piston (3) advances towards the first end (4), friction between the blocking surfaces (13c, 14c) causes the intermediate conical part (34) to advance slightly towards the first end (4). As a result, the conical external wall (35) presses against the internal wall of the body (2), causing the intermediate conical part (34) to increasingly press against the piston (3), thereby increasing the friction between the blocking surfaces (13c, 14c). A cyclical phenomenon is therefore caused, resulting in a blocking between said blocking surfaces (13c, 14c) that prevents the piston (3) from advancing towards the first end (4). The piston (3) may be unblocked simply by pulling it rearward, in other words, in a direction towards the second end (5) of the body (2). This embodiment allows the piston (3) to be blocked in any longitudinal position in relation to the body (2), thereby allowing a gradual vacuum to be created, where said vacuum may be varied in a continuous manner between the minimum and maximum volume.

Optionally, the device may be pre-loaded with a substance suitable for the type of treatment that is to be performed with the device. For example, it may be pre-loaded with an anticoagulant in the event that blood is to be extracted to the device. The invention contemplates pre-charging during the manufacture of the device or by the user themselves, depending on requirements.

FIGS. 16 and 17 respectively show a perspective view and a sectional view of an eighth embodiment of the device according to the invention, the section having been performed according to a vertical section plane containing the central longitudinal axis of the device. As in previous embodiments, the device (40) comprises a body (41) and a longitudinally movable piston (42). FIG. 17 shows that the piston (42) again comprises a rod (43) and a head (44). The rod (43) is connected to the head (44) by means of a threaded connection (45) and therefore can become connected and disconnected from the head (44). The head (44) is composed of a head body (46) and a cover (47). As in previous embodiments, the body (41) of the device (40) is again provided with a first end (48) at which there is a conduit (50) that communicates with an inner space (51) of the body (41), located between the piston (42) and the conduit (50), with the outside of the body (41). Also, the body (41) comprises a second end (49) through which the rod (43) of the piston (42) projects outward. As in previous embodiments, the piston (42), more specifically the head (44) of the piston (42), comprises blocking surfaces (52) intended to become engaged with corresponding blocking surfaces (53) on the second end (49) of the body (41) when the piston (42) is fully pulled back inside the body (41) towards the second end (49); said engagement is not shown in FIG. 17 because the piston (42) has been depicted only half way between the first end (48) and the second end (49). The body (41) of the device (40) further comprises a sealing member (54) adapted to sealingly close the conduit (50) of the first end (48). The device (40) also comprises a handle (55) to assist in the action of pulling the piston (42) rearward, i.e. towards the second end (49) of the body (41), and to help push the piston (42) forward, i.e. towards the first end (48) of the body (41). In this case, the handle (55) is not disconnectable, but rather forms an integral part of the body (41).

Figure 18:
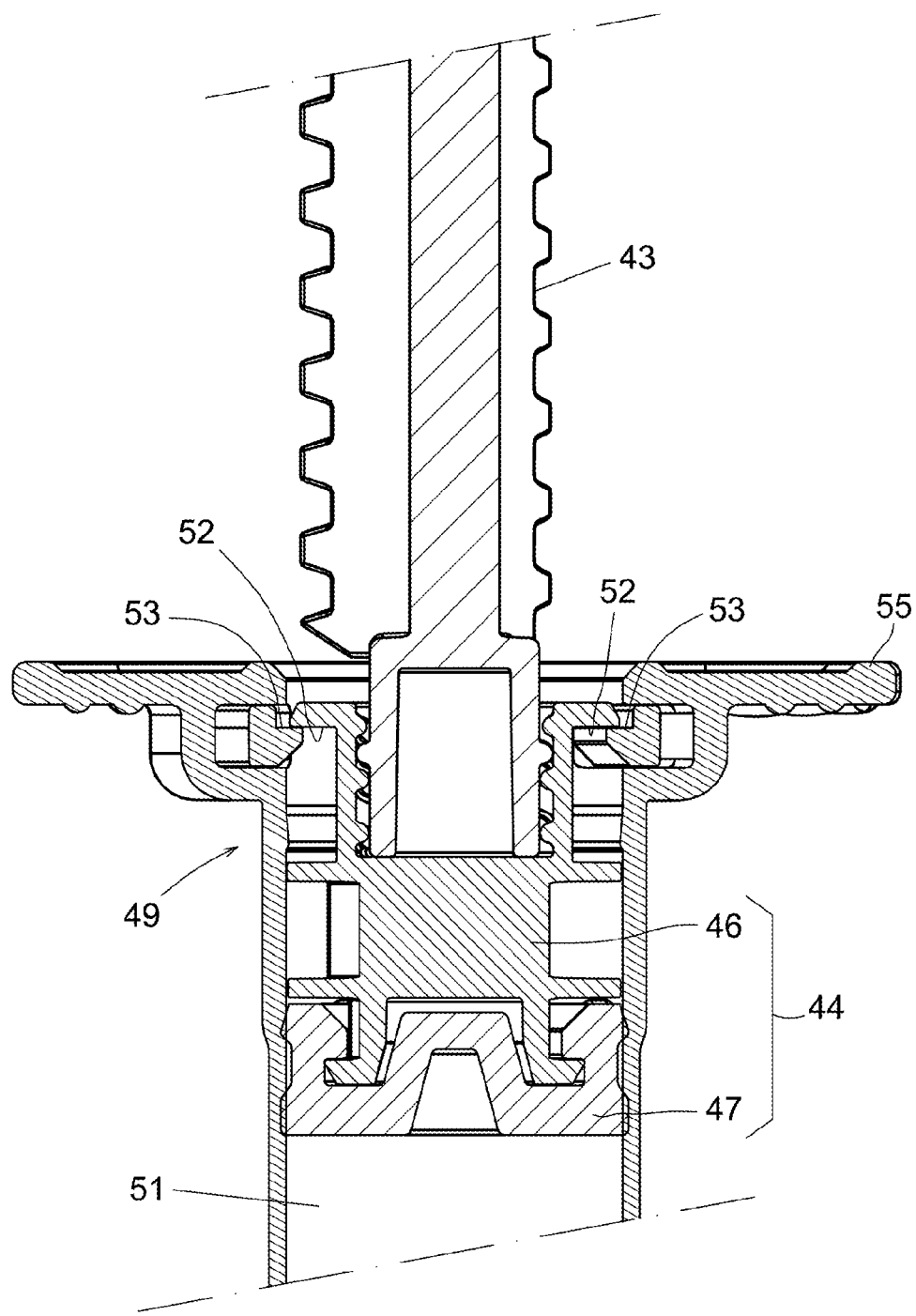
FIG. 18 shows an enlarged sectional view of the second end of the body of FIG. 17.

FIG. 18 shows an enlarged sectional view of the second end (49) of the body (41) of the previous figure, now shown in a situation in which blocking surfaces (52) of the head body (46) are engaged with the blocking surfaces (53) of the bodugy (41), offering a resistance to the forward movement of the piston (42) towards the first end (48). In the present embodiment, blocking surfaces (52) are inner elastic arms capable of slightly moving radially as shown by arrows in the figure, and elastically and radially driven towards the inside, in order to provide a clicking effect when the user pulls the piston (42) rearward far enough to reach the situation shown in the figure. The clicking effect provides an indication to the user that vacuum has been successfully achieved inside the device.

Figure 19:
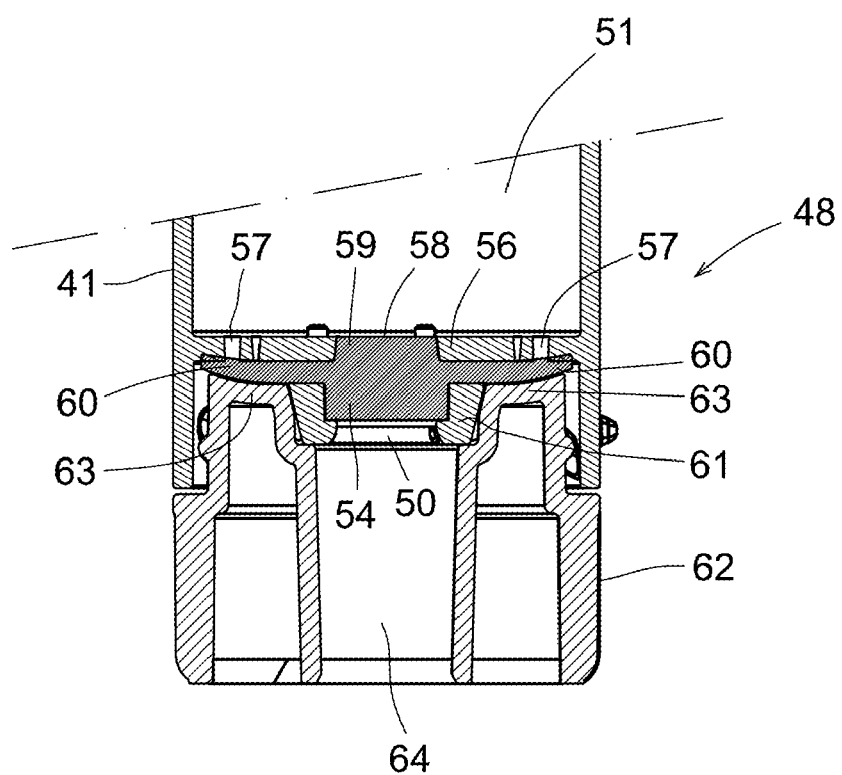
FIG. 19 shows an enlarged sectional view of the first end of the body of FIG. 17.

FIG. 19 shows an enlarged sectional view of the first end (48) of the body (41). In the area closer to the first end (48), the internal space (51) is delimited by a transversal inner wall (56) that has one or more through holes (57, 58). A central through hole (58) is occupied and closed by a central area (59) of the sealing member (54), said sealing member (54) being shaped like a disc. Other through holes (57) are free and externally closed by an outer area (60) of the sealing member (54). These other through holes (57) are conceived to allow the passing of fluid from the internal space (51) towards the outside under certain conditions that will be explained later. On the face of the sealing member (54) opposite to inner wall (56), a trunco-conical inner bushing (61) is arranged. Said inner bushing (61) has an inner through hole that is partially occupied by the central area (59) of the sealing member (54)—said central area (59) being fit into the through hole—and partially free, said free part being part of the conduit (50). On a different plane than the section plane, the inner bushing (61) is attached to the rest of the body (41) so that the inner bushing (61) keeps the sealing member (54) in place. The device further comprises a cap (62) that closes the first end (48) of the body (41). Said cap (62) has inner surfaces (63) adapted to press the outer area (60) of the sealing member (54) against the through holes (57), closing the holes. In other words, when the cap (62) is fastened as shown in the figure, a sandwich arrangement is formed in which the sealing element (54) is held between the inner wall (56) and, on the outside, the inner bushing (61) and the inner surfaces (63) of the cap (62). The outer area of the cap (62) can allow connecting other devices, as is the case of the present embodiment where said outer area is a luer-lock type connection having a central bore (64) in communication with the conduit (50). In this respect, it is contemplated that the cap (62) can have different designs to allow connecting various devices. The device, in the situation shown in the figure, therefore works as the previous embodiments: the conduit (50) that communicates the internal space (51) with the outside is closed by the sealing member (54), and the sealing member (54) allows for sealingly insertion of a needle towards the internal space (51).

Figure 20:
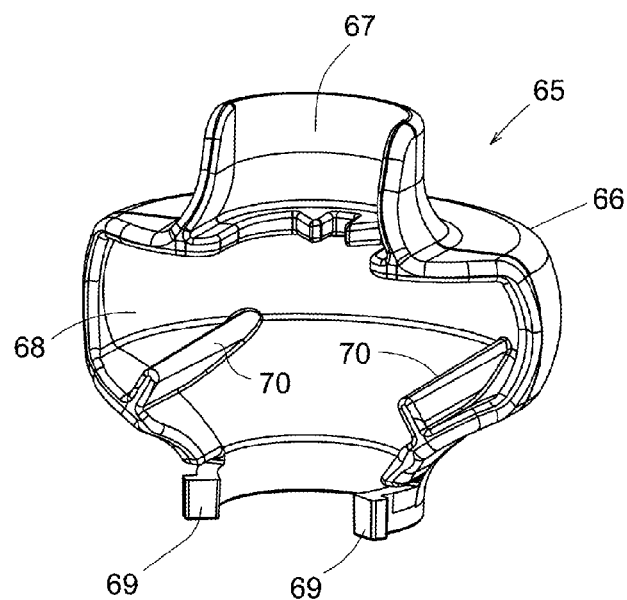
FIG. 20 shows an optional outer casing.
Figure 21:
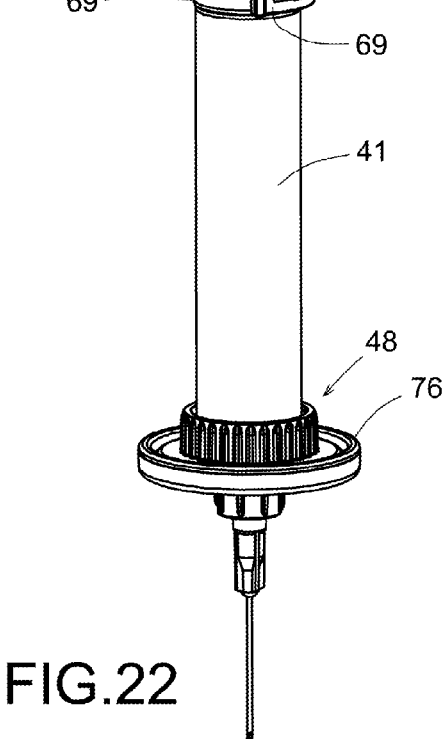
FIG. 21 shows an optional inner wheel.

The device of the present embodiment optionally comprises some additional components shown in FIGS. 20 and 21. Specifically, FIG. 20 shows an outer casing (65) adapted to fasten to the second end (49) of the body (41). The outer casing (65) comprises a body (66) that has a longitudinal through hole (67) designed to embrace the body (41) of the device and an inner space (68) shaped as a radial widening of the longitudinal through hole (67). The outer casing (65) further comprises elastic arms (69), curved inward with a curvature greater than the curvature of the outer walls of the body (41) of the device, in order to provide a clipping of the outer casing (65) onto the body (41). Finally, the outer casing (65) comprises inner protuberances (70) adapted to longitudinally contact inner walls of the body (41) of the device and with the handle (55), as will be shown later. In turn, FIG. 21 shows an inner wheel (71), provided with a threaded through hole (72) to allow the device's piston rod (43) to pass, as will be shown, and also provided with an outer face (73) that has slight protuberances (74), a rugosity or ruggedness to help cause the inner wheel (71) to turn by turning the outer face (73) with the user's fingers. Finally, the inner wheel (71) comprises angularly-spaced visual marks (75) that provide a reference to the user.

Figure 22:
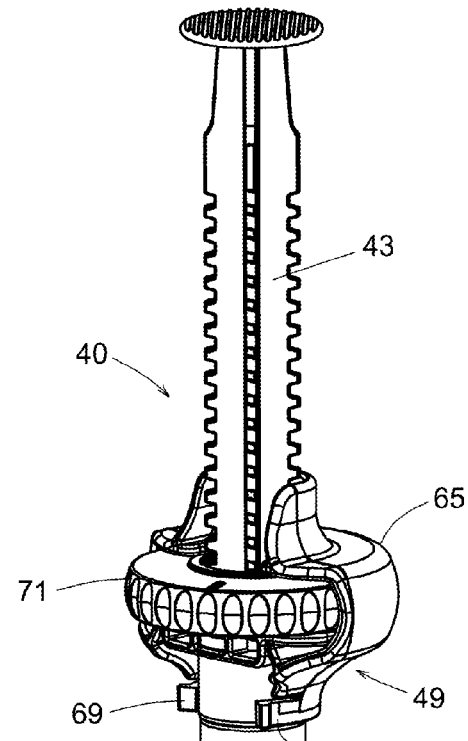
FIG. 22 shows the device of FIG. 16, once the inner wheel of FIG. 21 and the outer casing of FIG. 20 have been assembled.

FIG. 22 shows the device (40) of FIG. 16, having fastened the inner wheel (71) and the outer casing (65). The rod (43) has an outer threaded contour whose thread is compatible with the thread of the threaded through hole (72) of the inner wheel (71). The inner wheel (71) has therefore been connected by threading the rod (43) through the inner through hole (72) of the inner wheel (71) and onto the head (44). Once the inner wheel (71) has been set in place, the outer casing (65) has been radially coupled to the inner wheel (71), the inner wheel (71) becoming housed in the inner space (68) of the outer casing (65). The outer casing (65) has then finally been clipped to the body (41) by means of elastic arms (69).

Figure 23:
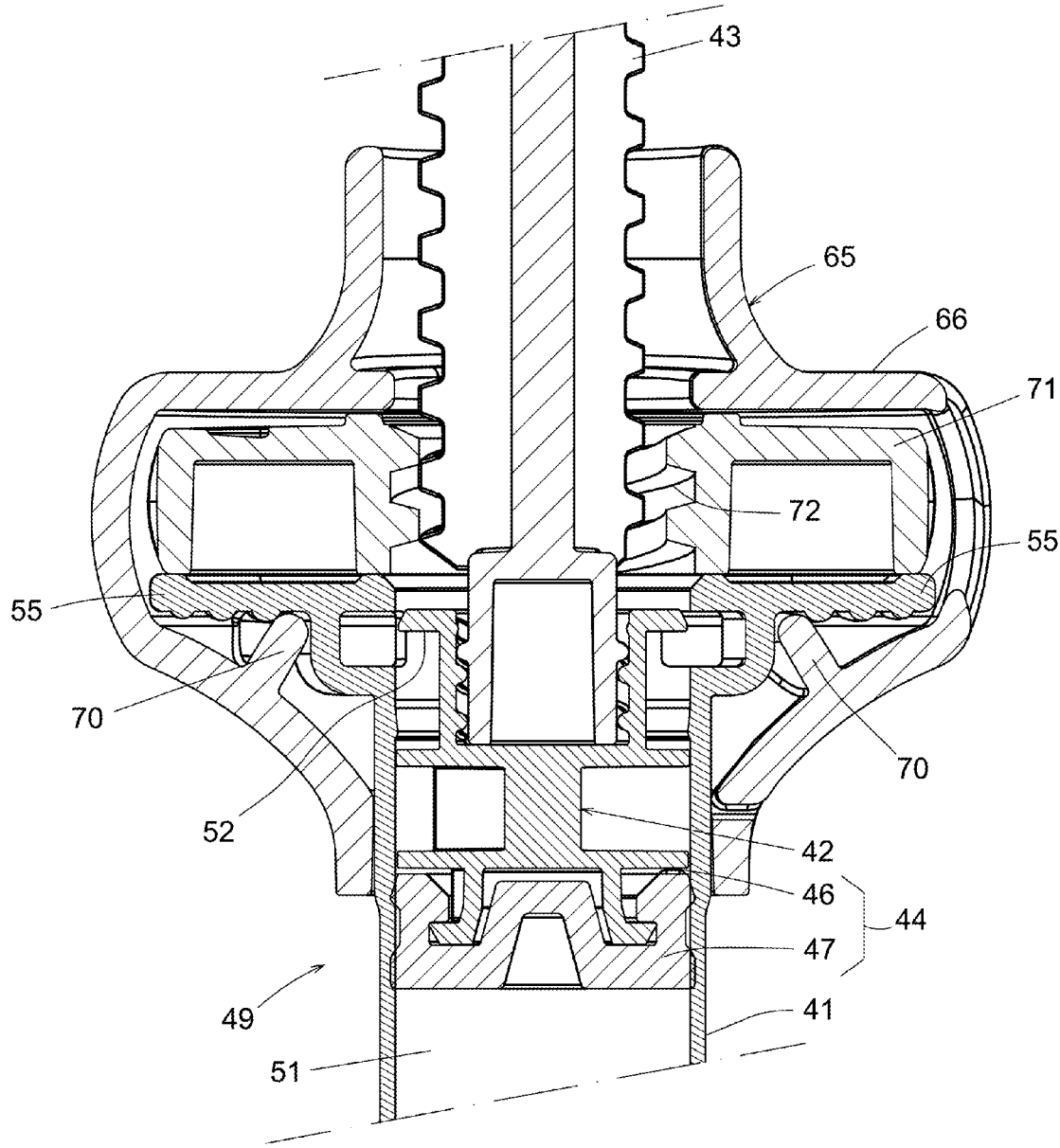
FIG. 23 shows an enlarged longitudinal sectional view of the area of the second end of the body of FIG. 22.

FIG. 23 shows an enlarged sectional view of the area of the second end (49) of the body (41) of the previous figure, in order to illustrate the functionality of the outer casing (65) and the inner wheel (71). In the situation of the figure, the piston (42) has been rotated enough for the blocking surfaces (52) to become freed, as shown in the sectional view, this present sectional view having been performed according to a different longitudinal section plane than that of FIG. 17. Outer casing (65) is connected to the body (41) insuch a way that outer casing (65) is unable to move longitudinally. For instance, in the present embodiment, outer casing (65) is unable to move longitudinally in one direction due to the presence of the inner wheel (71) and unable to move in the opposite direction due to the longitudinal contact between the protuberances (70) and the device handle (55). The inner wheel (71) is also restricted from moving longitudinally, due to the fixed presence of the outer casing (65) and the handle (55). Thus, when the user turns the inner wheel (71), because the thread of the threaded through hole (72) at least partially matches the outer thread of the rod (43), the rod (43) is caused to move longitudinally in a forward or rearward direction. The device therefore allows for simple and comfortable application of a liquid or other product contained in the internal space (51), as the user only needs to turn the inner wheel (71) to cause a forward movement of the piston (42), and thus a forward movement of the liquid towards the first end (48) of the body. The visual marks (75) help deliver exact liquid doses, as the angular distance between visual marks (75) is directly related to the longitudinal displacement of the piston (42), and therefore to the volume of liquid extracted from the device.

Figure 24:
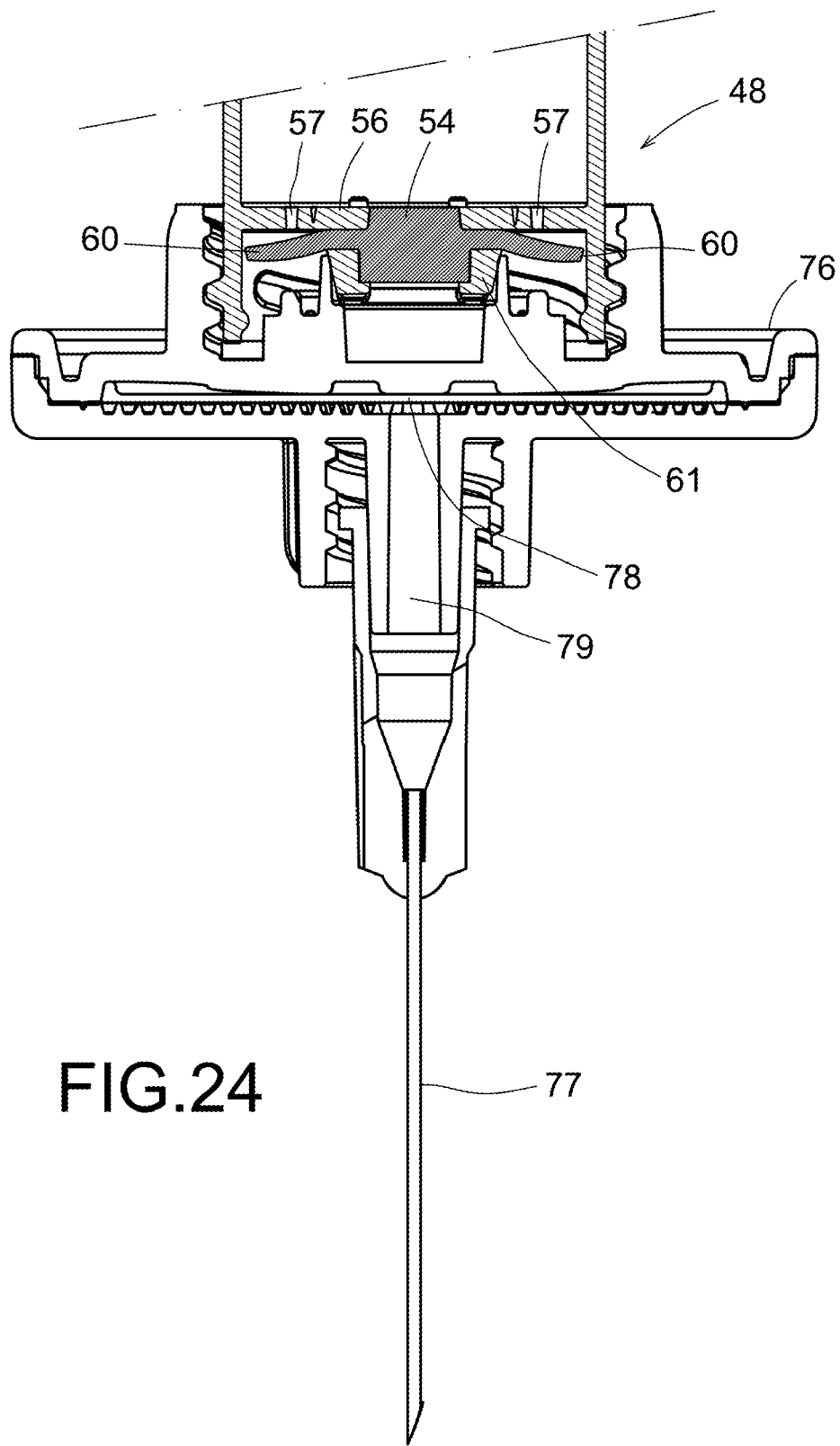
FIG. 24 shows an enlarged longitudinal sectional view of the area of the first end of the body of the device of FIG. 22.

The device of FIG. 22 is ready to be used to apply a liquid contained inside, for which the cap (62) has been removed and replaced by a filter accessory (76) provided with a needle (77). FIG. 24 shows a longitudinal sectional view of the first end (48) of the body (41) and the filter accessory (76). In this case, the needle (77) of the filter accessory (76) does not perforate the sealing member (54) of the device in order to provide an outlet for liquid to exit. Instead, the sealing member (54) outer area (60), no longer in contact with the cap (62), can shift longitudinally in relation to the through holes (57) of the inner wall (56). When the user causes the piston (42) to move forward, liquid pressure in the through holes (57) increases and pushes the outer area (60), eventually causing it to separate from the through holes (57) and allow liquid to exit via the through holes (57). In this particular embodiment, for instance, liquid then flows through one or more internal conduits of the filter accessory (76), not shown, passes through a filtering membrane (78) that retains impurities, and exits through the inner conduit (79) of the needle (77). In other words, according to the invention, the device automatically opens when the cap (62) is removed, partially freeing the sealing member (54), and the user applies enough force on the piston (42) for the liquid pressure to increase and slightly open the sealing member (54).

The invention claimed is:

1. A device for extracting, storing and/or processing blood or other substances of human or animal origin, and for applying blood compounds or other biological compounds, comprising:
    a hollow body;
    a piston arranged longitudinally movably inside said body;
    the body comprising a first end at which a conduit is provided connecting an internal space of the body located between the piston and the conduit with the outside of the body, and a second end comprising an opening through which the piston projects outward from the body, said second end being hermetically separated from the internal space by means of the piston, wherein:
    part of the piston is configured to be reversibly or irreversibly separated and removed from the rest of the device through said opening of said second end so that a remaining portion of the piston does not project out of the body, wherein
    the piston comprises at least one blocking surface,
    the body comprises at least one blocking surface configured to come into contact with a blocking surface of the piston and thereby offer resistance to the piston advancing towards the first end while allowing the piston to freely move back towards the second end, where
    the device further comprises a perforable sealing member arranged at or proximate the conduit, providing an airtight closing of the conduit,
    wherein the piston is configured to move towards the second end of the body, such that a vacuum is formed within the internal space by the hermetical separation of the internal space and the second end by the piston, and by the airtight closing of the conduit by the perforable sealing member.

2. The device according to claim 1, wherein the sealing member is internal to the body.

3. The device, according to claim 1, wherein the sealing member is external and connectable to the first end.

4. The device according to claim 1, wherein the piston is capable of moving rotationally inside the body, and wherein at least one blocking surface of the body and at least one blocking surface of the piston are arranged so that blocking occurs only in certain rotational positions of the piston in relation to the body, the piston being free in relation to the body in the remaining rotational positions.

5. The device according to claim 4, wherein at least one blocking surface of the piston is comprised in a tab that projects radially from the piston and wherein at least one corresponding blocking surface of the body is comprised in a transversal seating surface, the body presenting internal walls, the distance of which to the longitudinal central axis decreases in the direction of rotation in which the piston must rotate to unblock from the body so that when the rotation of the piston is caused in said direction the tabs rotate in contact with the internal walls and are flexed until the piston is unblocked in relation to the body.

6. The device, according to claim 1, further comprising a handle on the second end of the body to enable the action of causing the piston to move back towards said second end, the handle being removably connected to the body.

7. The device, according to claim 1, wherein the piston comprises at least one breakable area so that the piston may be dismantled manually into separate parts.

8. The device, according to claim 7, further comprising a pusher member that features a first area capable of pushing the piston so that the first area may overcome the resistance to the advance of the piston offered by blocking between at least one blocking surface of the piston and the corresponding blocking surface of the body, and cause the advance of the piston towards the first end.

9. The device, according to claim 8, wherein the piston is capable of moving rotationally inside the body, and wherein at least one blocking surface of the body and at least one blocking surface of the piston are arranged so that blocking occurs only in certain rotational positions of the piston in relation to the body, the piston being free in relation to the body in the remaining rotational positions, and wherein the first area of the pusher member is capable of being connected to the piston in such a way that the pusher member can cause the piston to rotate.

10. The device, according to claim 8, wherein the first area of the pusher member is provided with a shape complementary to that of the piston so that the connection between the pusher member and the piston is caused by pushing of the pusher member.

11. The device, according to claim 8, wherein the first area of the pusher member is provided with a shape with a mechanical connection to the piston so that the connection between the pusher member and the piston both allows the piston to be pushed towards the first end and the piston to be pulled, causing piston to move back towards the second end.

12. The device, according to claim 1, wherein the piston comprises a rod and a head, where the rod is fixed to the head by a connectable and disconnectable joint.

13. The device, according to claim 12, wherein at least one blocking surface of the piston is comprised in the head of the piston, so that when a corresponding blocking surface of the body is blocked on said blocking surface of the head the rod of the piston may be disconnected maintaining the blocking between the head and the body.

14. The device, according to claim 12, wherein the joint between the rod and the head is threaded in a certain direction, and wherein the body presents at least one stopper member against an area of the head is configured to come into contact when the head rotates in a direction opposite to said certain direction, thus allowing the rod to be unthreaded from the head.

15. The device, according to claim 14, wherein
the piston is capable of moving rotationally inside the body, and wherein at least one blocking surface of the body and at least one blocking surface of the piston are arranged so that blocking occurs only in certain rotational positions of the piston in relation to the body, the piston being free in relation to the body in the remaining rotational positions,
wherein at least one blocking surface of the piston is comprised in a tab that projects radially from the piston and wherein at least one corresponding blocking surface of the body is comprised in a transversal seating surface, the body presenting internal walls, the distance of which to the longitudinal central axis decreases in the direction of rotation in which the piston must rotate to unblock from the body so that when the rotation of the piston is caused in said direction the tabs rotate in contact with the internal walls and are flexed until the piston is unblocked in relation to the body, and
wherein the area of the head that comes up against the stopper member is comprised in a tab.

16. The device, according to claim 1, wherein the piston comprises a blocking surface capable of coming into contact with a blocking surface located on the internal wall of an intermediate conical part of the body, wherein said intermediate conical part presents limited longitudinal mobility in relation to the piston and in relation to the rest of the body, and wherein when the piston advances towards the first end a friction between the blocking surfaces causes the intermediate conical part to slightly advance towards the first end and to be pressed against the piston, thereby increasing the friction and enabling the vacuum in the internal space to be adjusted in a continuous manner.

17. The device, according to claim 1, wherein the internal space is delimited, in the area nearest to the first end, by a transversal inner wall provided with one or more through holes that are closed by an outer area of the sealing member, and the device further comprises a cap that closes the first end of the body, wherein said cap comprises inner surfaces configured to press the outer area against the through holes and close said through holes, wherein in the absence of the cap the outer area of the sealing member is longitudinally movable so that a high enough increase of the pressure of a fluid contained in the internal space can cause the outer area to separate from the through holes.

18. The device, according to claim 1, further comprising an outer casing that at least partially covers an inner wheel externally threaded onto a rod of the piston, where the outer casing and the inner wheel present no relative longitudinal movement with respect to the body, and a turn of the inner wheel causes a longitudinal movement of the rod.

19. The device according to claim 1, further comprising an outer jacket covering at least partially inside a wheel to the externally threaded shaft where the outer jacket and the inner wheel do not have a longitudinal movement relative to the body so that a rotation of the inner wheel causes longitudinal displacement of the shaft.

* * * * *